United States Patent
Kuo et al.

(10) Patent No.: US 10,925,261 B2
(45) Date of Patent: Feb. 23, 2021

(54) **METHOD FOR INDUCING FEMINIZATION IN *TILAPIA AUREA* VIA IMMERSION WITH ETHINYL ESTRADIOL**

(71) Applicants: GALLANT OCEAN INTERNATIONAL, INC., Kaohsiung (TW); Chien-Hsien Kuo, Chiayi (TW)

(72) Inventors: Chien-Hsien Kuo, Chiayi (TW); Yueh-Yuan Hsu, Kaohsiung (TW); Chung-Jian Huang, Kaohsiung (TW)

(73) Assignees: GALLANT OCEAN INTERNATIONAL, INC., Kaohsiung (TW); Chien-Hsien Kuo, Chiayi (TW)

( * ) Notice: Subject to any disclaimer, the term of this patent is extended or adjusted under 35 U.S.C. 154(b) by 354 days.

(21) Appl. No.: 15/939,673

(22) Filed: Mar. 29, 2018

(65) Prior Publication Data

US 2019/0297856 A1 Oct. 3, 2019

(51) Int. Cl.
*A01K 61/10* (2017.01)
*A61K 31/57* (2006.01)

(52) U.S. Cl.
CPC .............. *A01K 61/10* (2017.01); *A61K 31/57* (2013.01); *A01K 2207/35* (2013.01)

(58) Field of Classification Search
CPC ....................................................... A01K 61/10
See application file for complete search history.

(56) References Cited

PUBLICATIONS

Gennotte et al., Molecular Reproduction & Development, 2014, 81(12):1146-1158.*
Gennotte et al., Journal of Experimental Zoology, Part A: Ecological Genetics and Physiology, 2015, 323(1): 31-38.*

* cited by examiner

*Primary Examiner* — Rei Tsang Shiao
(74) *Attorney, Agent, or Firm* — Hamre, Schumann, Mueller & Larson, P.C.

(57) ABSTRACT

A method for inducing feminization in *Tilapia aurea* includes subjecting *Tilapia aurea* aged 1 to 3 dph to an immersion treatment with ethinyl estradiol in a concentration ranging from 142 to 200 ppm for 1 to 3 minutes.

5 Claims, No Drawings

METHOD FOR INDUCING FEMINIZATION IN *TILAPIA AUREA* VIA IMMERSION WITH ETHINYL ESTRADIOL

FIELD

The disclosure relates to a method for inducing feminization in *Tilapia aurea*, and more particularly to a method for inducing feminization in *Tilapia aurea* using an immersion treatment with ethinyl estradiol.

BACKGROUND

*Tilapia* is a type of freshwater fish from the Cichlidae family, and due to its advantages of fast-growth, high reproductive rate, good adaptability, and omnivorous nature, tilapia has become the world's top harvested fish in the aquaculture industry. Common tilapia species for fish farming include *Oreochromis niloticus* (also known as Nile tilapia) and *Oreochromis aureus* (also known as *Tilapia aurea*).

When male and female tilapia are placed together for farming, their growth rate is slow due to energy consumption caused by natural reproduction. In addition, the increased number of offspring due to natural reproduction causes an overly high density of fish in the aquaculture pond, which leads to growth stagnation. Therefore, mono-sex culture is widely utilized in breeding tilapia to solve this issue. Under mono-sex culture, the growth rate and the weight of male fish are twice compared to female fish. As a result, a committed goal of this field is to increase the production of male tilapia.

Although male *Tilapia aurea* have a relatively small size, when male *Tilapia aurea* (ZZ♂) mate with female Nile tilapia (XX♀) (interspecific hybridization), all-male tilapia hybrids (XZ♂) having a relatively large size are obtained. Therefore, there is a need to develop a method for increasing the production of male *Tilapia aurea* offspring in the aquaculture industry.

On the other hand, the feeding of an estrogen to induce feminization of *Tilapia aurea* has been studied. The percentage of male offspring can be increased by mating the resulting feminized *Tilapia aurea* (ZZΔ♀) with male *Tilapia aurea* (ZZ♂). For example, as disclosed in Melard (1995), Aquaculture, 130:25-34, ethinylestradiol (also known as 17α-ethynylestradiol) was dissolved in 95% ethanol, and the resulting solution was added into fish feed to obtain fish feed respectively containing 100, 150 and 200 mg/kg of ethinyl estradiol. *Tilapia aurea* fish fry were respectively fed with these three kinds of feed for 40 days. Experimental results showed that the feminization rates (i.e. the percentage of females) of the *Tilapia aurea* obtained respectively via feminization induction with 100, 150, and 200 mg/kg of ethinyl estradiol were 94%, 93% and 98%. Melard further mated the feminized *Tilapia aurea* with male *Tilapia aurea*, and the resulting percentage of male offspring ranged between 68% and 100%. Since the percentage of male offspring varied in a considerable range, the male *Tilapia aurea* offspring was not produced in a consistently effective manner.

The induction of feminization in *Tilapia aurea* by estrogen feeding requires a long period of time, and might be negatively affected by poor palatability and uneven estrogen distribution, hence causing difficulty in ensuring that all the fish fry have an adequate intake of estrogen. Therefore, the development of a rapid and convenient method for inducing stable feminization in *Tilapia aurea* is in demand.

SUMMARY

Therefore, an object of the present disclosure is to provide a method for inducing feminization in *Tilapia aurea* that can alleviate at least one of the drawbacks associated with the prior art.

The method includes subjecting *Tilapia aurea* aged 1 to 3 dph (days post-hatch) to an immersion treatment with ethinyl estradiol in a concentration ranging from 142 to 200 ppm for 1 to 3 minutes.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

In order to develop a rapid and convenient immersion process for stable feminization induction, the applicants found that immersion of *Tilapia aurea* fry at a particular age with 142 to 200 ppm of ethinyl estradiol for a short period of time is consistently effective in inducing feminization.

Therefore, the present disclosure provides a method for inducing feminization of *Tilapia aurea*, which includes subjecting *Tilapia aurea* aged 1 to 3 dph (days post-hatch) to an immersion treatment with ethinyl estradiol in a concentration ranging from 142 to 200 ppm for 1 to 3 minutes.

In certain embodiments of the present disclosure, the *Tilapia aurea* subjected to the immersion treatment is 3 dph of age.

In certain embodiments of the present disclosure, the concentration of ethinyl estradiol is 200 ppm.

According to the present disclosure, the immersion treatment can be carried out at a temperature ranging from 25° C. to 30° C. In an exemplary embodiment of the present disclosure, the immersion treatment is carried out at 25° C.

According to the present disclosure, feminized *Tilapia aurea* (ZZΔ♀) (namely, F1 generation) obtained according to the method of the present disclosure can be mated with wild-type male *Tilapia aurea* (ZZ♂) to obtain all-male *Tilapia aurea* (ZZ♂) (namely, F2 generation). The all-male *Tilapia aurea* (ZZ♂) can be used directly as food, or can be used to produce all-male tilapia hybrids (XZ♂) with the following process. First, masculinized Nile tilapia (XX♂) obtained using a technique commonly used in the art are mated with wild-type female Nile tilapia (XX♀) to obtain all-female Nile tilapia (XX♀). Following which, the all-female Nile tilapia (XX♀) are mated with the all-male *Tilapia aurea* (ZZ♂) (namely F2 generation), to obtain all-male tilapia hybrids (XZ♂) (namely, F3 generation).

The present disclosure will be further described in the following examples. However, it should be understood that the following examples are solely intended for the purpose of illustration and should not be construed as limiting the present disclosure in practice.

EXAMPLES

Experimental Materials 1.3 Dph *Tilapia aurea* Fry

Males and females of *Tilapia aurea* (about 12 months of age) provided by Prof. Chien-Hsien Kuo from the Department of Aquatic Biosciences at National Chiayi University (Taiwan) served as the parent fish in the following example. The male and female fish were separately raised in concrete ponds provided with water maintained at 25° C. and about 6 mg/L of dissolved oxygen under natural light, and were provided with feed ad libitum. Mating was carried out with a male-to-female ratio of 2:5. Fertilized eggs were flushed out from the oral cavity of the female fish to be collected, followed by incubation at 25° C. for 7 to 14 days. 3 dph fish fry were obtained.

Example 1. Induction of Feminization in *Tilapia aurea* Via Immersion Treatment with Ethinyl Estradiol Two immersion solutions respectively having ethinyl estradiol concentrations shown in Table 1 below were each prepared as follows. An appropriate amount of ethinyl estradiol was dissolved in 10 mL of ethanol, followed by mixing with 5 L of water in a water tank.

5 trials of feminization induction were conducted using a respective one of the two immersion solutions. Specifically, for each trial of feminization induction, the 3 dph *Tilapia aurea* fry (the amount thereof is shown in Table 1) were placed in the respective immersion solution at 25° C. for 3 minutes. Following which, the induced fish fry were placed in a water tank equipped with an oxygen-enriched equipment for breeding. After seven months of breeding, the gender of all the surviving fish was observed, and the feminization rate (i.e. the percentage of females) was calculated.

Results:

The resulting feminization rate is shown in Table 1.

TABLE 1

Concentrations of ethinyl estradiol, number of fish fry, and resulting feminization rate in each trial

| Trial | Concentration of ethinyl estradiol (ppm) | Number of fish fry | Feminization rate (%) |
|---|---|---|---|
| 1 | 200 | 506 | 100 |
| 2 | | 300 | 100 |
| 3 | | 421 | 100 |
| 4 | | 367 | 100 |
| 5 | 142.85 | 300 | 87 |

As shown in Table 1, the feminization rate of each trial is equal to or higher than 87%. In particular, when the concentration of ethinyl estradiol applied is 200 ppm, the feminization rate up to 100% can be achieved. In comparison, in the case that no estrogen is used to conduct feminization induction, the feminization rate of offspring resulting from mating between male and female fish should be theoretically 50%. The result of this experiment shows that the immersion treatment using ethinyl estradiol in a concentration ranging from 142.85 to 200 ppm can effectively induce feminization of *Tilapia aurea* fry at a particular age in a short period of time.

In addition, the applicants further mated the feminized *Tilapia aurea* obtained by immersion with 200 ppm of ethinyl estradiol (i.e. obtained from Example 1) with male *Tilapia aurea* in a female-to-male ratio of 5:2, and the resulting percentage of male offspring is as high as 95% to 100%. Such result shows that feminized *Tilapia aurea* obtained using the feminization induction method of the present disclosure can be applied for producing all-male *Tilapia aurea* in a consistently effective manner.

All patents and literature references cited in the present specification as well as the references described therein, are hereby incorporated by reference in their entirety. In case of conflict, the present description, including definitions, will prevail.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, FIGURE, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for inducing feminization of *Tilapia aurea*, comprising:
   subjecting *Tilapia aurea* aged 1 to 3 dph (days post-hatch) to an immersion treatment with ethinyl estradiol in a concentration ranging from 142 to 200 ppm for 1 to 3 minutes.

2. The method of claim 1, wherein the *Tilapia aurea* is aged 3 dph.

3. The method of claim 1, wherein the concentration of ethinyl estradiol is 200 ppm.

4. The method of claim 1, wherein the immersion treatment is carried out at a temperature ranging from 25° C. to 30° C.

5. The method of claim 4, wherein the immersion treatment is carried out at 25° C.

* * * * *